United States Patent [19]

Altura et al.

[11] Patent Number: 5,696,125
[45] Date of Patent: Dec. 9, 1997

[54] SUBSTANCE ABUSE-INDUCED HEMORRHAGIC STOKE IN AN ANIMAL MODEL

[75] Inventors: Burton M. Altura; Bella T. Altura, both of Beechhurst, N.Y.

[73] Assignee: Research Foundation of the State University of New York, Albany, N.Y.

[21] Appl. No.: 393,756

[22] Filed: Feb. 24, 1995

[51] Int. Cl.$^6$ .................... A61K 31/515; A61K 31/44; A61K 31/445; A61K 31/135; A61K 31/045
[52] U.S. Cl. .................... 514/270; 514/282; 514/288; 514/317; 514/654; 514/724
[58] Field of Search .................... 514/270, 724, 514/282, 288, 317, 654

[56] References Cited

PUBLICATIONS

Chem. Abst. 96:135534, Hosobuchi et al., 1982.
Altura et al, Alcohol Intoxication Results in Rapid Loss in Free Magnesium in Brain and Disturbances in Brain Bioenergetics: Relation to Cerebrovaospasm, Alcohol–Induced Strokes, and Barbiturte Anesthesia–Induced Deaths, *Magnesium and Trace Elements*, 1991–92; 10:122–135.
Altura et al, Cardiovasular Risk Factors and Magnesium: Relationships to Atherosclerosis, Ischemic Heart Disease and Hypertension, *Magnesium and Trace Elements*; 1991–92, 10:182–192.
Altura et al, Role of Brain [Mg$^{2+}$]$_i$ in Alcohol–Induced Hemorrhagic Stroke in a Rat Model: A $^{31}$P–NMR in Vivo––Study, *Alcohol*, vol. 12, No. 1, pp. 1–6 (galley proof), 1995.
Donahue et al, Alcohol and Hemorrhagic Stroke, *JAMA*, May 2, 1986, vol. 255, No. 17, pp. 2311–2314.
Altura et al, Ethanol Promotes Rapid Depiction of Intracellular Free Mg in Cerebral Vascular Smooth Muscle Cells; Possible Relation to Alcohol–Induced Behavioral and Stroke–Like Effects, *Alcohol*, 10:563–566, 1993.
Chutkow, J.G. Metabolism of Magnesium in the Central Nervous System: Relationship Between Concentrations of Magnesium in Cerebrospinal Fluid and Brain in Magnesium Deficiency, *Neurology*, 24:180–187, 1974.
Hillbom et al, Does Ethaanol Intoxication Promote Brain Infarctions in Young Adults?, *LancetII*: 1181–1183;1978.
Anonymous, Binge Drinking and Stroke, *Lancet* ii:660–661, 1983.
Camargo, C.A. Jr., Moderatre Alcohol Consumption and Stroke, *Stroke*, 20:1611–1626, 1989.
Riverea, L.I.et al, Effects of Elevated Plasma Magnesium Concentration on Cerebrospinal Fluid Levels of Magnesium in Neonatal Swine, *Proc. Soc. Exp. Biol. Med.*, 197:98–101, 1991.
Altura et al, Alcohol–Induced Spasms of Cerebral Blood Vessels: Relation to Cerebrovascular Accidents and Sudden Death, *Science*, 220:331–333, 1983.

Nishio, A. et al, Comparative Vasodilator Effects of Magnesium Salts on Rat Mesenteric Arterioles and Venules, *Arch. Intern Pharmacodyn. Ther.*, 298:139–163, 1989.
Kaste, M. et al, Alcohol Intoxication: A Risk Factor for Primary Subarachnoid Hemorrhage, *Neurology* 32:706–711, 1982.
Alture, B. M. et al. Alcohol, The Cerebral Circulation, and Strokes, *Alcohol* 1:325–331, 1984.
Altura, B.M. et al, Cocaine Induces Intracellular Free Mg Deficits, Ischemia and Stroke as Observed by in Vivo $^{31}$P–NMR of The Brain, *Biochem. Biophys. Acta Membr.* 1111:271–273, 1992.
Zhang, A. et al, Ethanol–Induced Contraction of Cerebral Arteries in Diverse Mammals and its Mechanism of Action, *Eur. J. Phramacol.*, 248:229–236, 1993.
Gupta, R.K. et al, $^{31}$P–NMR Studies of Intracellular Free Mg$^2$ in intact Frog Skeletal Muscle, *J. Biol. Chem.* 225:3987–3993, 1980.
Gupta, R.K. et al, NMR Studies of Intracellular Metal Ions Intact Cells and Tissues, *Ann. Rev. Biophys.* 13:221–246, 1984.
Lee, K., Alcoholism and Cerebrovascular Thrombosis in the Young, *Acta Neurol. Scand.* 59:270–274, 1979.
Altura, B.M. et al, Deficits in Brain–CSF Magnesium Result in Cerebrovasospasm and Rupture of Cerebral Microvessels: Possible Relation to Stroke, *Clin. Res.* 39:394A, 1991.
Rasmussen, H.S., The Electrophysiological Effects of Intravenous Magnesium on Human Sinus Node, Atrioventricular Node, Atrium and Ventricle, *Clin. Cardiol.* 12:85–90, 1984.
Jacobus, W.E. Intracellular Acidosis and Contractility in the Normal and Ischemic Heart as Examined by $^{31}$P–NMR, *J. Mol. Cell. Cardiol.*, 14(Suppl. 3):13–20, 1982.
Flink, E.B. Magnesium Deficiency in Alcoholism, *Alcohol Clin. Exp. Res.* 10:590–594; 1986.
Altura, B.M. et al, Role of Magnesium and Calcium in Alcohol–Induced Hypertension and Strokes as Probed by in Vivo Television Microscopy, Digital Image Microscopy, Optical Spectroscopy, $^{31}$P–NMR, Spectroscopy and a Unique Magnesium Ion–Selective Electrode, *Alcohol Clin. Exp. Res.*, vol. 18(5), pp. 1057–1068, Oct. 1994.
Altura, B.M. et al, Alcohol, Stroke, and the Cerebral Circulation, *Alcohol Health & Research World*, vol. 14, No. 4, 1990.
Zou et al, Beneficial Effects of High Magnesium on Alcohol–Induced Cardiac Failure, *Magnes Trace Elem*, 1991–92; 10:409–419.

*Primary Examiner*—Raymond Henley, III
*Attorney, Agent, or Firm*—Morgan & Finnegan

[57] ABSTRACT

The present invention is an substance-induced-hemorrhagic stroke animal model. The substance-induced-hemorrhagic stroke animal model is useful in screening therapeutics for the prevention and/or treatment of stroke. The present invention also encompasses magnesium salt for the prevention and treatment of stroke.

15 Claims, 2 Drawing Sheets

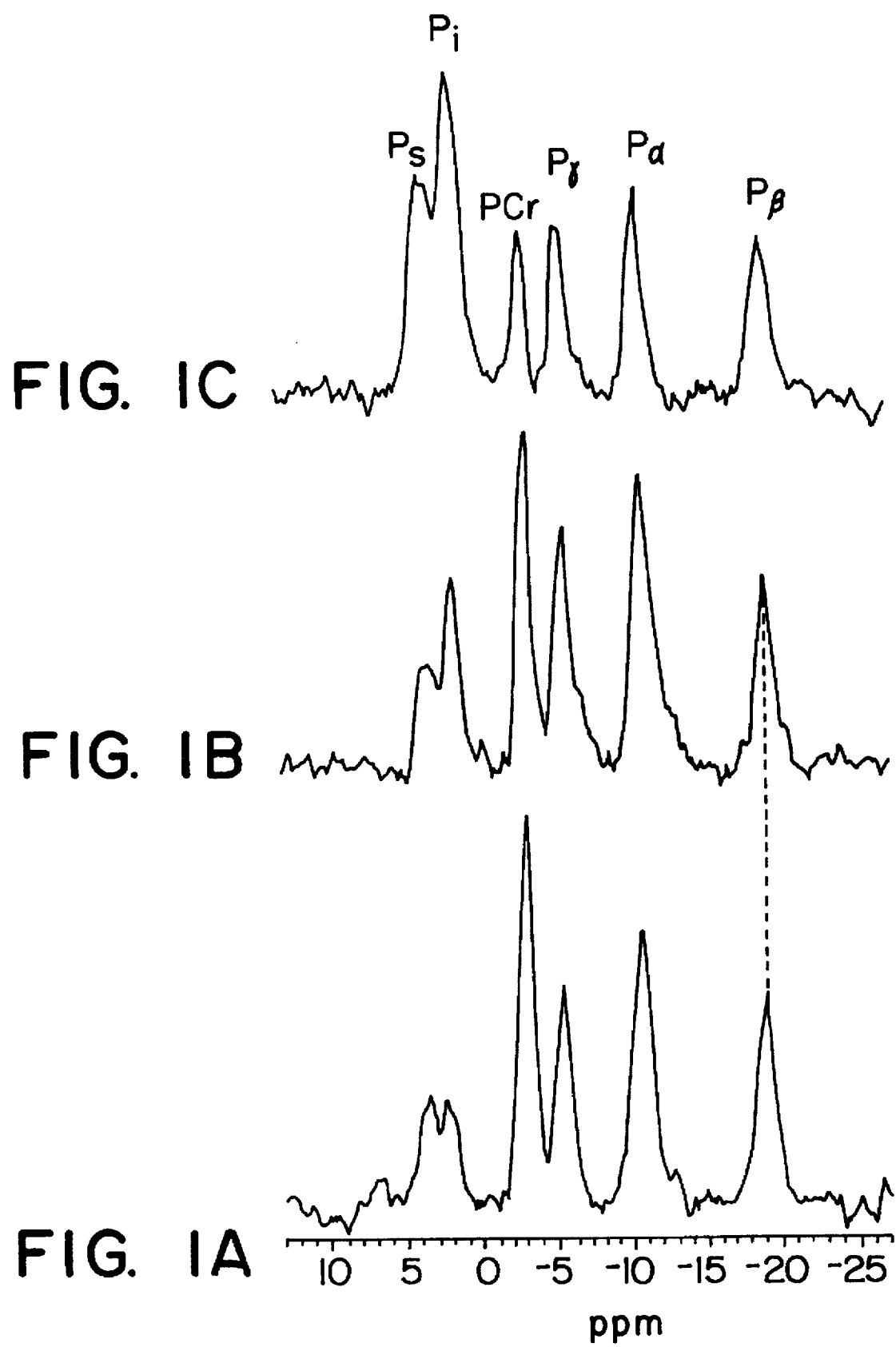

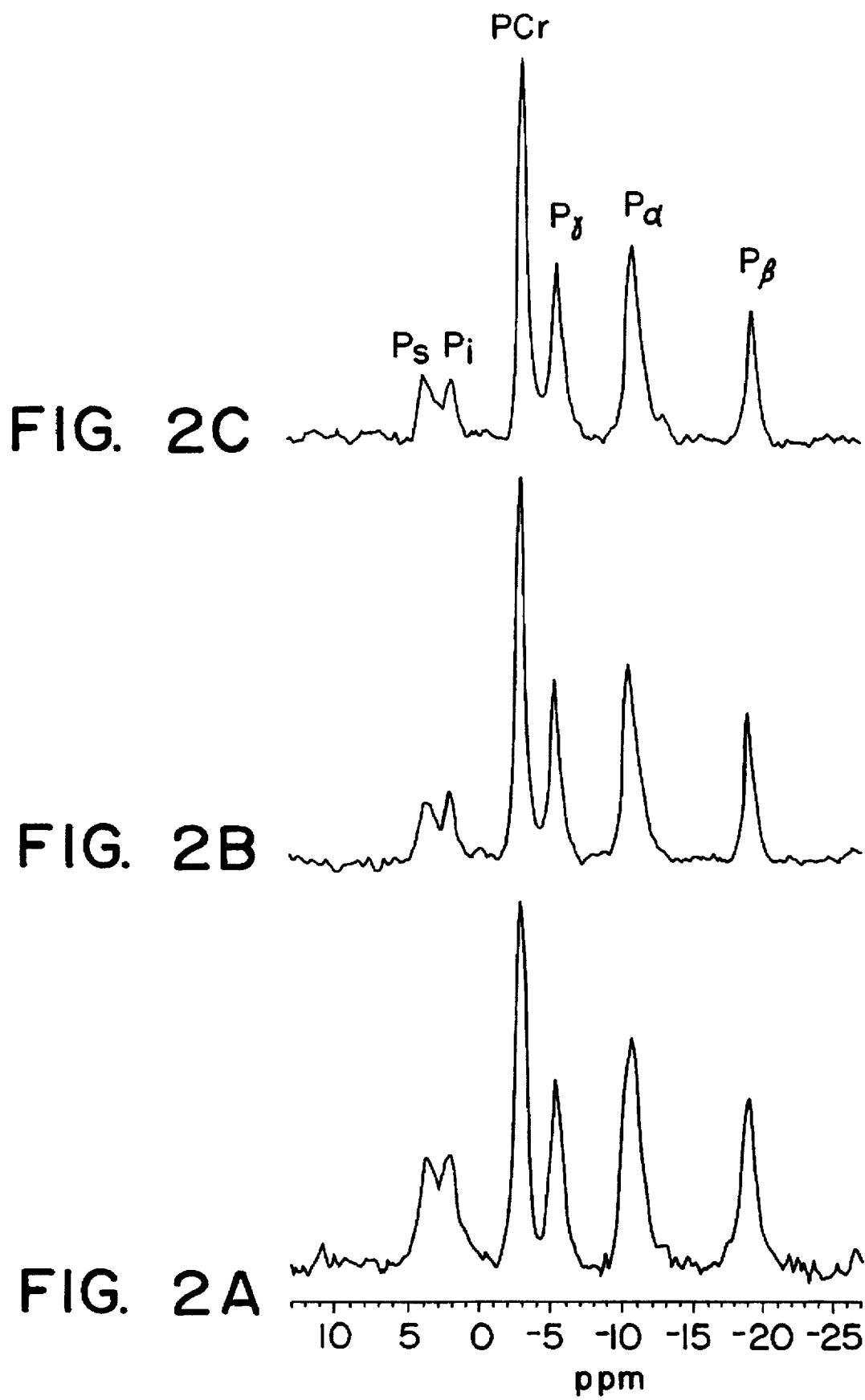

SUBSTANCE ABUSE-INDUCED HEMORRHAGIC STOKE IN AN ANIMAL MODEL

This invention was made with government support with Grant Number AA 08674 awarded by the National Institute of Alcoholism and Alcohol Abuse at the National Institutes of Health. The government has certain rights in the invention.

BACKGROUND OF THE INVENTION

Despite its reputation as a beverage that can be used socially, acute "binge-drinking" of alcohol (e.g., more than 80 g ingested in <24 h) is associated with an ever-growing number of strokes and sudden death. This type of "binge-drinking" has been shown to result in intracerebral and subarachnoid hemorrhages as well as cerebral infarction (2, 3, 12, 17, 22–24). Onset of symptoms can occur within minutes to hours after this type of drinking. Particularly alarming are the increasing number of reports suggesting that even moderate alcohol elevates the risk of both intracerebral and subarachnoid hemorrhage (3,14). Although it is certain that alcohol "binge drinking" is a clear risk for stroke, it is by no means certain how these strokes are brought about (2, 3, 12, 14, 17, 22–24). Moreover, to our knowledge an animal model for alcohol-induced hemorrhagic stroke is not available. It has been reported that 10% of rats administered alcohol IP, in various doses (0.2–6.6 g/kg), developed hemorrhagic like strokes upon autopsy of the brain (6). Interestingly, this is about the incidence seen in the human experience (2, 3, 12, 14, 17, 22–24).

Using direct in vivo microcirculatory studies on the rat brain, it has been shown previously that ethanol can induce concentration-dependent contractions of cerebral arterioles and venules followed by rupture of cerebral microvessels. The concentration range (10–500 mg/ml) used parallels that needed for its graded effects of euphoria, mental haziness, muscular incoordination, stupor, stroke, and coma in humans (5) Recent, preliminary in-situ observations on the rat brain indicate that perfusion of the cortical microcirculation with artificial cerebral spinal fluid containing reduced extracellular $Mg^{3+}$([$Mg^{2+}$]) can result in spasms of arterioles and venules followed by rupture of venules and postcapillaries, leading to focal hemorrhages and brain edema (7). These results are, thus, very similar to that observed with administration of ethanol in normal, $Mg^{2+}$-sufficient brain preparations. Since it has long been known that chronic alcohol intake can deplete the human body of Mg (18), we hypothesized that alcohol-induced loss of $[Mg^{2+}]_i$ should precipitate cerebral vasospasm resulting in hypoxia, ischemia, and stroke in the brain, provided the dose of ethanol simulates the high doses in the human experience. In addition, Mg-pretreatment of such susceptible animals, which would yield $[Mg^{2+}]_o$ concentrations in the blood higher than normal, should protect against acute alcohol-induced stroke.

SUMMARY OF THE INVENTION

The present invention is a stroke animal model. A method is provided that induces stroke in a mammal. In one aspect of the invention, the animal model is a model for substance abuse-induced hemorrhagic stroke.

The present invention encompasses a method of monitoring progression of stroke and for monitoring therapies for the prevention or treatment of substance abuse-induced hemorrhagic stroke.

Another aspect of the invention is a method of prevention and treatment of substance abuse-induce hemorrhagic stroke.

A further aspect of the invention is a method for screening therapeutics useful in preventing or treating stroke using an animal model.

Yet another aspect of the invention is a pharmaceutical composition useful in preventing or treating stroke.

BRIEF DESCRIPTION OF THE DRAWINGS

FIGS. 1A–1C. $^{31}$P-NMR spectra of rat brain showing ethanol-induced alterations in $[Mg^{3+}]_i$, pH, [PCR], and $P_i$. Spectra represent control animal (FIG. 1A), 5 min after injecting ethanol (6.6 gm/kg) IP (FIG. 1B) and 12 min after injecting ethanol (6.6 gm/kg) (FIG. 1C). $^{31}$P resonances of phosphoryl groups of ATP (Pα, Pβ, Pγ), phosphocreatine (PCr), inorganic phosphate ($P_1$) and sugar phosphates ($P_2$) are labeled. The vertical line shows the position of the Pβ resonance before ethanol administration. Between 5 and 12 min, the animal underwent hemorrhagic stroke, evidenced by extensive bleeding in the brain upon autopsy.

FIG. 2A–2C. $^{31}$P-NMR spectra of rat brain showing protection by 4 μmol/min IV $MgCl_2$ infusion against ethanol-stroke dose (6.6 gm/kg, IP). These spectra indicate a failure of alcohol in the presence of high plasma $[Mg^{2+}]_o$ to induce any change in brain $[Mg^{2+}]_i$, $pH_i$, [PCr] and $P_i$. Symbols similar to those in FIG. 1. Spectra represent $Mg^{2+}$ treated control (FIG. 2A); 5 min after injecting ethanol (6.6 gm/kg,IP) in presence of high plasma $[Mg^{2+}]$ (FIG. 2B); and 60 min after injecting the alcohol stroke dose (FIG. 2C).

DETAILED DESCRIPTION OF THE INVENTION

The present invention is a stroke animal model. The stroke is induced in the animal by treatment with a stroke-inducing agent or combination of agents. Of particular interest as stroke-inducing agents are substance abuse agents. Substance abuse agents include but are not limited to ethyl alcohol, cocaine, metabolites of cocaine, crack cocaine, hallucinogens, derivatives thereof, and the like. Various hallucinogens which may be used to induce stroke include but are not limited to lysergic acid diethylamide (LSD), phencyclidine hydrochloride (PCP), opiods, normorphine, morphine, amphetamine, methamphetamines, barbiturates, cannabinoids and derivatives thereof.

The stroke-inducing substance is provided to the an animal, preferably a mammal, in an amount sufficient to induce a stroke in the animal. Stroke is defined herein as intracranial or intracerebral bleeding or cerebral infarctions. The progression of the stroke is monitored by $^{31}$P-NMR spectrometry using an NMR spectrometer such as GE-omega 400 WB with 9.4 Tesla. Brain-free magnesium$^{2+}$, intracellular pH, [PCr]/[ATP], [$P_1$]/[ATP] ratios were determined using ⁻P-NMR spectroscopy. In conjunctions with these measurement in the brain, other parameters may be measured such as plasma ionized magnesium, plasma total magnesium, plasma ionized calcium, plasma sodium and plasma potassium concentrations.

In one embodiment of the stroke animal model of the present invention, the animal, preferably a mammal, is immobilized, preferably lightly anesthetized with a barbiturate or derivatives thereof, and the like, which are known in the art. In one embodiment, the animal is anesthetized using pentobarbital sodium.

The barbiturate is administered by appropriate routes known in the art such as intravenous (I.V.), intraperitoneal (I.P.), intramuscularly (I.M.), intracranial (I.C.) and the like. In one embodiment, the barbiturate is provided I.M.

The stroke animal model of the present invention characteristically demonstrates profound subarachnoid and intracranial bleeding after treatment with the stroke-inducing agent, combinations of stroke-inducing agents, or with the stroke-inducing agent in combination with a barbiturate.

The stroke animal model of the present invention characteristically have low brain ionized magnesium concentrations in the range of about 200 to about 325 μmolar compared to a normal brain ionized magnesium concentration of about 550 to about 900 μmolar. A brain ionized magnesium concentration of about 275 μmolar±20% or lower is predictive of a stroke in the animal model.

The stroke animal of the present invention also shows low intracellular brain pH of about 6.85–6.98 or lower.

In the case of alcohol as the stroke-inducing agent, the amount of alcohol sufficient to induce a stroke in the animal is about 6 to about 8 gm/kg, preferably about 6.5 to about 7 gm/kg body weight.

In the case of cocaine as the stroke-inducing agent, the amount of cocaine hydrochloride, crack cocaine or metabolites thereof sufficient to induce a stroke in the anesthetized animal model is about 1 to about 25 mg/kg. These levels of the stroke-inducing cocaine hydrochloride or metabolites thereof are comparable to levels in humans of about 1–10 mg per liter of blood concentration.

The stroke-inducing agent may be administered by routes known in the art. In one embodiment the route of administration is I.P.

The stroke animal model is useful in screening therapeutic drugs for the prevention or treatment of stroke in animals, preferably mammals, more preferably humans. Of particular interest are therapeutic drugs for the prevention or treatment against stroke-inducing agents particularly substance abuse agents such as ethyl alcohol, cocaine and metabolites thereof, crack cocaine, hallucinogens, derivatives thereof and the like. For use in screening, the animal may be immobilized as described above. In the case of prevention of a stroke the therapeutic agent is provided prior to the administration of the stroke-inducing agent. In the case of treatment, the therapeutic agent is provided prior to, during, or after administration of the stroking inducing agent. Various concentrations may be administered in order to determine the effective dose of the therapeutic drug.

Therapeutics that can be screened using the animal model of the present invention included but are not limited to magnesium salts and mixtures thereof, lazaroids, NMDA receptor antagonists, free radical scavengers, mannitol, steroids, glucocorticoids and the like. Therapeutic drugs or combination of drugs may be formulated into pharmaceutical compositions with pharmaceutically acceptable carrier.

Another aspect of the invention is a method of preventing or treating substance abuse-induced hemorrhagics stroke in animals, preferably mammals, more preferably humans. In this method of treatment, magnesium salt or mixture thereof, lazaroids, NMDA receptor antagonists, free radical scavengers, mannitol, steroids, glucocorticoids and the like is administered to the animal in an amount sufficient to prevent or lessen the severity of the stroke. In one embodiment, the amount of magnesium salt is also sufficient to increase the brain ionized magnesium concentration as measured by $^{31}$P-NMR spectroscopy. In another embodiment, the amount of magnesium salt is sufficient to increase or stabilize the plasma ionized magnesium concentration at least 2 fold, preferably about 2 to about 3 fold compared to a normal plasma ionized magnesium concentration.

In one method of treating stroke, the magnesium salt is provided at a concentration of about 4 μmol/min, or about 4 to about 10/μmol/min I.V.

In one embodiment the magnesium salt is in the form of magnesium sulfate (MgSO$_4$). Other magnesium salts that are useful in the present invention include but are not limited to MgCl, MgCl.6H$_2$O, MgSO$_4$.7H$_2$O, and other magnesium salts that are highly water soluble, highly bioavailable and safe for human use. The magnesium salt is provided as a pharmaceutical composition in a pharmaceutically acceptable carrier.

The present invention is a substance abuse-induced hemorrhagic stroke model which closely resembles the syndrome seen clinically. The present invention includes Mg$^{2+}$ pretreatment, in a dose which does not affect mean arterial blood pressure, which prevents substance abuse-induced hemorrhagic stroke in the majority of animals so treated, despite the fact that the very significant elevation of plasma ionized and total Mg did not seem to alter brain [Mg$^{2+}$], ph$_1$, or phosphometabolites, in normal, control rats. It does seem clear from these $^{31}$P-NMR data that alcohol-induced and cocaine-induced strokes are associated with a very rapid fall in brain [Mg$^{2+}$]$_1$, and preceded by significant alterations in brain pH$_1$, [PC]/[ATP], and [P$_1$]. Although some Mg$^{2+}$ protected animals exhibited only a slight fall in brain [Mg$^{2+}$], the stroke-alcohol dose failed to result in any changes in pH$_1$ [PCr]/[ATP] or [P$_1$]. Similarly, observations have been noted in 60–70% of animals stroked with cocaine HCl.

The consistent drops in pH, and [PCr]/[ATP] together with the marked elevation of [P$_1$] prior to death, indicates that alcohol-induced and cocaine-induced cerebral ischemia is preceded by deficits in brain [Mg$^{2+}$]$_1$. These findings point to a vasospastic response in cerebral microvessels leading to vascular occlusion and intracerebral, as well as subarachnoid, bleeding set into motion by a loss of cerebral vascular smooth muscle and neuronal [Mg$^{2+}$]$_1$ (6,9,13). All contractile events in muscle tissue are mediated by an increase in the cytoplasmic level of free calcium ions (CaD, and alcohol and cocaine probably releases Ca$^{2+}$ for contractility in cerebral vascular smooth muscle (3,5,30). It is known that Mg$^{2+}$ normally either gates or has an action on Ca$^{2+}$ entry and intracellular release of Ca$^{2+}$ (1,4,29,31). Thus, depletion of [Mg$^{2+}$]$_1$ by alcohol and cocaine in cerebral vascular smooth muscle (9), and neuronal tissue (13), would allow entry and intracellular release of Ca$^{2+}$ causing contraction. The progressive, irreversible rise in [H$^+$]$_1$ and [P$_1$] and the associated loss in [PCr] would be consistent with this hypothesis. It is of some interest here to note that another abused substance, viz., cocaine, which has also been demonstrated to produce strokes and cerebral ischemia is also associated with a rapid loss of brain [Mg$^{2+}$]$_1$, rises in [H$^+$] and [P$_1$] and loss of [PCr] (8,10).

Some attention should be devoted to the observations reported, herein, on the failure of high plasma [Mg$^{2+}$]$_0$ to affect brain [Mg$^{2+}$]$_1$, pH$_i$ or phosphometabolites in normal, healthy rats. Although previous workers have investigated the effects of elevated plasma levels of [Mg$^{2+}$]$_0$ on brain total Mg contents (15,16), and total Mg content in cerebral spinal fluid in animals and patients (27,28), which have provoked controversy, the present invention measured free ionized Mg both in the brain and plasma. A high dose of Mg infusion (10 μmol/min) was utilized to be certain that plasma Mg would be elevated rapidly. Failure of the Mg infusion at the higher dose to elevate brain-free Mg further supports our data at the lower dose of Mg (i.e., 4 μmol/min). Rather significant elevation in $[Mg^{2+}]_o$, which is often seen in treated preeclamptic and eclamptic patients (26), does not result in significant changes in brain $[Mg^{2+}]_i$ despite the possibility it may change total Mg content (15,16). Only the ionized Mg is physiologically active. While not being bound by theory, there is the possibility that although elevation in plasma $[Mg^{2+}]_i$ may not actually result in elevation in brain $[Mg^{2+}]_i$, it could act on endothelial cell surface membranes to regulate $Ca^{2+}$ influx (and its intracellular release) (31) and set into motion intracellular signals to the underlying cerebral vascular smooth muscle cells, which result in cerebral vasocilation (3,4) thus increasing cerebral blood flow, tissue oxygenation and nutrient delivery.

EXAMPLE 1

Male Wistar rats, weighing 142–208 g, were anesthetized lightly with pentobarbital sodium (Nembutal, Park Davis, Ann Arbor, Mich., 3 mg/100 g, IM). A right-sided femoral arterial catheter was placed for monitoring arterial blood pressure (in select animals) and a femoral vein catheter (PE20, Clay-Adams) for infusion of either normal, isotonic saline, or $MgCl_2$ (4 or 10 μM/min) at 0.04 ml/min using an Harvard (Harvard Apparatus, Cambridge, Mass.) constant infusion pump. Femoral arterial blood pressure was monitored with a physiological pressure transducer (Statham P23Db, Puerto Rico). In some experiments, normal saline or $MgCl_2$, was infused IV for 30–45 min prior to administration of ethanol (6.6 g/Kg) IP or cocaine HCl (5–10 mg/kg) and prior to placement in the NMR spectrometer. In other experiments, normal saline or $MgCl_2$ was infused IV for 2 h (no ethyl alcohol or cocaine administered) after the animals were placed in a Bruker-General Electric Omega 400 WB spectrometer with a 9.4 T vertical bore magnet utilizing double-tuned $^{31}P/^1H$ RF coils (6,8). Body temperature was maintained by keeping the gradient coils at 30°–32° C. and by placing a blanket around each animal. The animal was carefully accommodated in the NMR probe (with head pointing down) so that all of the brain was contained within the RF coil. To make certain the brain was positioned properly, proton images were obtained using S50 gradient coils. After obtaining control $^{31}P$-NMR spectra (prior to ethyl alcohol or cocaine HCl or saline) each animal was removed from the NMR probe and carefully injected IP with ethyl alcohol or cocaine HCl (dissolved in normal physiological saline). Each alcohol-, or cocaine HCl, or saline-injected animal was then returned to the NMR probe and repeat $^{31}P$-NMR spectra were obtained at various intervals of time (e.g., 3–120 min, or up until death had occurred).

Brain-free $Mg^{2+}$ was measured from the $^{31}P$-chemical shifts of ATP resonances. The chemical shift difference between the α- and β-phosphoryl group resonances of ATP ($\delta\alpha\beta$), along with a knowledge of the apparent $K_d$ of MgATP (50 μmol/L at pH 7.2, 37° C.) under intracellular ionic conditions, was used to determine the concentration of $[Mg^{2+}]_i$ (8,9,20):

$$\phi = \frac{\delta_{\alpha\beta}^{H} - \delta_{\alpha\beta}^{MgATP}}{\delta_{\alpha\beta}^{ATP} - \delta_{\alpha\beta}^{MgATP}}$$

-continued $$[Mg^{2+}]_i = K_d \left( \frac{[1]}{\phi} - 1 \right)$$

The $K_d^{MgATP}$ was corrected for varying pH (8,9,20). In a typical $^{31}P$-NMR spectrum of in vivo brain, the signal-to-noise ratio was 100 and the widths of the ATP resonance lines were approximately 200 Hz. A Monte Carlo simulation was used to estimate the error of the NMR chemical shift measurement under these conditions and yields a standard deviation of 4 Hz (6,8).

Intracellular pH ($pH_i$) was measured from the $^{31}P$-NMR spectra; the protonation state, hence chemical shift of the intracellular phosphate (Pi) resonance, is pH-dependent and allows $pH_i$ to be calculated by use of the following equation (20,21):

$$pH_i = 6.73 + \log (\delta_{obs} - 2.90 \, V_P)/(5.70 V_P - \delta_{obs})$$

Where $V_P$ is the $^{31}P$ Larmor frequency in MHz and $\delta_{obs}$ is the chemical shift difference between the Pi and P-creatinine (PCr) resonances in Hz.

The [PCr]/[ATP] and $[P_i]$/[ATP] concentration ratios were calculated from the ratio of integrated areas and corrected for partial saturation of resonance intensities (6,8).

In control animals, plasma ionized Mg ($IMg^{2+}$), total Mg, ionized calcium ($ICa^{2+}$), $Na^+$ and $K^+$ were measured. Plasma $IMg^{2+}$, $ICa^{2+}$, $Na^+$, and $K^{30}$ were determined with specific ion selective electrodes (ISE's) using a NOVA Biomedical State Profile 8 Analyzer (Nova Biomedical, Watham, Mass.) (11) as described in U.S. Ser. No. 07/864,646 filed Apr. 7, 1992 and U.S. Pat. No. 5,364,642, which are a continuation-in-part of U.S. Ser. No. 07/681,940 filed Apr. 8, 1991; total Mg was measured using atomic absorption (AA) spectrophometry and a Perkin-Elmer Zeeman 5000 AA spectrometer (CT) (11). For all of these determinations, heparinized blood samples (using <15 U/ml heparin sodium) were removed from a cannulated carotid artery under anaerobic conditions and centrifuged anaerobically for 10–15 min at 3000–4000 rpm. The ISE's yielded very precise measurements (CVs<5%) (6,11).

Where appropriate, mean values±SE were calculated and compared using paired t-tests, unpaired Student's t-tests, Chi-square, and ANOVA employing Scheffe's contrast test for multiple measurements. A p<0.05 was considered significant.

EXAMPLE 2

Continuous intravenous infusion of 10 μmol/min of $MgCl_2$, in normal control rats, lowered mean arterial blood pressure (5–25 mmHg), similar to previous reports (25), but failed to alter brain $[Mg^{2+}]_i$, $ph_i$, [PCr], [PCR]/[ATP] or $[P_1]$ up to 2 h (Table 1). This regimen of $MgCl_2$ elevated plasma $IMg^{2+}$ 400% and total plasma Mg threefold over normal; $ICa^{2+}$, $Na^+$ and $K^+$ were not altered, even after 2 h of constant $Mg^{2+}$ infusion (Table 1). Infusion of 4 μmol/min $MgCl_2$ did not affect mean arterial blood pressure significantly but also elevated plasma Mg threefold, i.e., from 0.72±0.005 to 2.13±0.004 mM/L (n=10, p<0.001); $ICa^{2+}$, $INa^+$ and $IK^+$ were not altered from control plasma levels.

TABLE 1

EFFECTS OF CONSTANT INTRAVENOUS INFUSION OF 10 μmol/min MAGNESIUM
CHLORIDE ON BRAIN $[Mg^{2+}]_i$, $pH_i$, AND INTRACELLULAR
PHOSPHOMETABOLITES AS WELL AS ON PLASMA ELECTROLYTES

| Group time-min (after $MgCl_2$) | $[Mg^{2+}]_i$ μM | $pH_i$ | [PCr] (mM) | $[P_i]$ (mM) | [PCr]/[ATP] | $[P_i]$/[ATP] | $[Mg^{2+}]_i$ (mM) | Total $Mg^†$ (mM) | $(Ca^{2+})e$ (mM) |
|---|---|---|---|---|---|---|---|---|---|
| Controls | 510 ± 22 | 7.27 ± 0.06 | 4.76 ± 0.30 | 1.26 ± 0.08 | 2.07 ± 0.13 | 0.55 ± 0.035 | 0.56 ± 0.027 | 0.98 ± 0.06 | 1.42 ± 0.04 |
| $MgCl_2$ | | | | | | | | | |
| 5 min | 446 ± 30 | 7.31 ± 0.11 | 3.62 ± 0.50 | 1.11 ± 0.17 | 1.57 ± 0.22 | 0.48 ± 0.075 | — | 1.93* ± 0.12 | — |
| 30 min | 460 ± 42 | 7.27 ± 0.10 | 4.19 ± 0.35 | 1.08 ± 0.17 | 1.82 ± 0.14 | 0.47 ± 0.074 | — | 2.59* ± 0.04 | — |
| 45 min | 479 ± 39 | 7.25 ± 0.02 | 4.81 ± 0.88 | 1.32 ± 0.23 | 2.10 ± 0.39 | 0.57 ± 0.10 | — | — | — |
| 90 min | 521 ± 38 | 7.13 ± 0.08 | 4.10 ± 0.34 | 1.07 ± 0.21 | 1.78 ± 0.15 | 0.46 ± 0.09 | 2.17* ± 0.058 | 2.99* ± 0.18 | 1.34 ± 0.035 |

Values are means ± SEM.
†Total plasma Mg.
*Significantly different from controls (p < 0.01).

Of six animals injected with 6.6 g/kg of pure ethanol IP, all died within 12 to 35 min after alcohol administration. Upon autopsy of the brain, each animal demonstrated profuse subarachnoid and intracerebral hemorrhages. We estimated that the intracranial cavity of each alcohol-stroked rat contained 2–3 ml of blood. However, all six animals receiving IV 4 μmol/min of $MgCl_2$ for 30–45 min., prior to ethanol, survived (p<0.01 compared to alcohol controls). Interestingly, most of the $Mg^{2+}$-treated (four of six) awakened from anesthesia-alcohol administration prior to the end of the 2 h of $MgCl_2$ infusion.

Of the six animals injected with alcohol, in the absence of $Mg^{2+}$ infusion, five different brains demonstrated consistently marked reductions (32%–69%) in measured $[Mg^{2+}]_i$ within 3–5 min after injection; the magnitude of the peak drop in $[Mg^{2+}]_i$ varied with the animal. But all but one of the alcohol-injected control animals exhibited a marked fall at 5 min (Table 2). Five minutes later, marked falls in $pH_i$ and in the [PCr]/[ATP] ratio were manifested (Table 2), followed by a sharp rise in the $P_i$ resonance concomitant with falls in [PCr] just prior to death (FIG. 1). Mean arterial blood pressure did not fall more than 5–8 mmHg until just before death.

Animals that received IV 4 μmol/min $Mg^{2+}$ pretreatment prior to 6.6 g/kg ethanol demonstrated only a slight fall in $[Mg^{2+}]_i$ (12%–18%) 10 min after alcohol; $[Mg^{2+}]_i$ remained close to normal brain levels for the 2 h of Mg infusion, despite the presence of a stroke-inducing dose of alcohol (FIG. 2). Neither brain [PCr], $[P_i]$, $pH_i$ nor the [PCr]/[ATP] ratio were altered in the $Mg^{2+}$-protected animals (FIG. 2). After sacrifice, two hr. later, autopsy of the brain failed to reveal any abnormalities or any signs of bleeding.

EXAMPLE 3

Cocaine-induced Stroke and Treatment

Rats under light anesthesia as described in Example 1 were injected I.P. with 10–25 mg cocaine HCl/kg body weight as a bolus injection. Animals were monitored as described above for 4 minutes to 2 hours. At the end of 2 hours 95% of the rats were dead.

In another group of rats, under light anesthesia, were infused I.V. for 30–45 minutes with $MgCl_2$ (4 or 10 uM/min) prior to a I.P. bolus injection of 10–25 mg cocaine HCl/kg body weight. Animals were monitored as described in

TABLE 2

INFLUENCE OF HIGH DOSE (6.6 g/kg) OF ALCOHOL ON CHEMICAL SHIFT
DIFFERENCE BETWEEN THE Pα AND Pβ RESONANCES OF ATP
AND THE $P_i$ AND PCr RESONANCES AS WELL AS THE
CALCULATED $[Mg^{2+}]_i$, $pH_i$ AND [PCr]/[ATP] IN RAT BRAIN

| Group time-min (after alcohol) | Chemical shift difference (Hz) Pα – Pβ | $P_i$ – PCr | $[Mg^{2+}]_i$ (μM) | $pH_i$ | [PCr]/[ATP] |
|---|---|---|---|---|---|
| Controls Alcohol | 1375.0 ± 4.2 | 817.2 ± 3.5 | 532 ± 70 | 7.24 ± 0.04 | 2.32 ± 0.12 |
| 5 min | 1399.9 ± 6.0* | 798.3 ± 8.3† | 302 ± 35† | 7.15 ± 0.09 | 2.18 ± 0.26 |
| 10 min | 1385.2 ± 3.0† | 761.7 ± 9.4† | 453 ± 29 | 6.98 ± 0.09† | 1.98 ± 0.10† |

Values are means ± SEM.
*Significantly different from controls (p < 0.01).
†Significantly different from controls (p < 0.05).

Examples 1 and 2. At the end of 2 hours, 60–70% of the animals were alive and had no indication or symptoms of stroke as monitored using the parameters described in Examples 1 and 2.

It is understood that the examples and embodiments described herein are for illustrative purposes only and that various modifications or changes in light thereof will be suggested to persons skilled in the art and are to be included within the spirit and purview of this application and scope of the appended claims.

The references and patents referred to are incorporated herein by reference.

REFERENCES

1. Altura, B. M.; Altura, B. T., Magnesium ions and contraction of vascular smooth muscle: Relationship to some vascular diseases. Fed. Proc. 40:2672–2679; 1981.
2. Altura, B. M.; Altura, B. T., Alcohol, the cerebral circulation, and strokes. Alcohol 1:325–331; 1984.
3. Altura, B. M.; Altura B. T., Alcohol, stroke, and the cerebral circulation. Alcohol Health Res. World 14:322–331; 1990.
4. Altura, B. M.; Altura B. T.; Carella, A.; Murakawa, T.; Nishio, A. $Mg^{2+}$-$Ca^{2+}$ interaction in contractility of vascular smooth muscle: $Mg^{2+}$ versus organic calcium channel blockers on myogenic tone and agonist-induced responsiveness of blood vessels. Can. J. Physiol. Pharmacol. 65:729–745; 1987.
5. Altura, B. M.; Altura, B. T.; Gebrewold, A. Alcohol-induced spasms of cerebral blood vessels: Relation to cerebrovascular accidents and sudden death. Science 220:331–333; 1983.
6. Altura, B. M.; Altura, B. T.; Gupta, R. K. Alcohol intoxication results in rapid loss in free magnesium in brain and disturbances in brain bioenergetics: Relation to cerebrovasospasm, alcohol-induced strokes, and barbiturate anesthesia-induced deaths. Magnes. Trace Elem. 10:122–135; 1992.
7. Altura, B. M.; Gebrewold, A.; Huang, Q. F.; Altura, B. T. Deficits in brain-CSF magnesium result in cerebrovasospasm and rupture of cerebral microvessels: Possible relation to stroke. Clin. Res. 39:394A; 1991.
8. Altura, B. M.; Gupta, R. K. Cocaine induces intracellular free Mg deficits, ischemia and stroke as observed by in vivo $^{31}$P-NMR of the brain. Biochim, Biophys. Acta Membr. 1111:271–273; 1992.
9. Altura, B. M.; Zhang, A.; Cheng, T. P. O.; Altura, B. T. Ethanol promotes rapid depiction of intracellular free Mg in cerebral vascular smooth muscle cells; Possible relation to alcohol induced behavioral and stroke-like effects. Alcohol 10:563–566; 1993.
10. Altura, B. M.; Zhang, A.; Cheng, T. P. O.; Altura, B. T. Cocaine induces rapid loss of intracellular free $Mg^{2+}$ in cerebral vascular smooth muscle cells. Eur. J. Pharmacol. 246:299–301; 1993.
11. Altura, B. T.; Altura, B. M. Measurement of ionized magnesium in whole blood, plasma and serum with a new ion-selective electrode in healthy and diseased human subjects. Magnes. Trace Elem, 10:90–98; 1992.
12. Anonymous. Binge drinking and stroke. Lancet ii:660–661; 1983.
13. Babu, A. R.; Cheng, T. P. O.; Zhang, A.; Altura, B. T.; Altura, B. M. Low concentrations of ethanol deplete astrocytes of intracellular free magnesium. Brain Res. Bull. (in press).
14. Camargo, C. A. Jr. Moderate alcohol consumption and stroke. Stroke 20:1611–1626; 1989.
15. Chol, W. W.; Warner, D. S.; Monaham, T.; Todd, M. M. Effects of acute hypermagnesemia on the threshold for lidocaine-induced seizures in rat. Am. J. Obstetr. Gynecol. 164:693–697; 1991.
16. Chutkow, J. G. Metabolism of magnesium in the central nervous system: Relationship between concentrations of magnesium in cerebrospinal fluid and brain in magnesium deficiency. Neurology 24: 180–187; 1974.
17. Donahue, R. P.; Abbott, R. D.; Reed, D. M.; Yano, K.. Alcohol and hemorrhagic stroke. JAMA 225:2311–2314; 1986.
18. Flink, E. B. Magnesium deficiency in alcoholism. Alcohol Clin. Exp. Res. 10:590–594; 1986.
19. Gupta, R. K.; Moore, R. D. $^{31}$P-NMR studies of intracellular free $Mg^{2+}$ in intact flog skeletal muscle. J. Biol. Chem. 255:3987–3993; 1980.
20. Gupta, R. K.; Gupta, P.; Moore, R. D. NMR studies of intracellular metal ions in intact cells and tissues. Ann. Rev. Biophys. Bioeng. 13:221–246; 1984.
21. Jacobus, W. E.; Pores, I. H.; Lucas, S. K.; Weisfeldt, M. L.; Flaherty, J. T. Intracellular acidosis and contractility in the normal and ischemic heart as examined by $^{31}$P-NMR. J. Mol. Cell. Cardiol. 14(Suppl. 3):13–20; 1982.
22. Hillborn, M. E.; Kaste, M. Does ethanol intoxication promote brain infarctions in young adults? Lancet ii: 1181–1183; 1978.
23. Kaste, M.; Hillborn, M. E. Alcohol intoxication: A risk factor for primary subarachnoid hemorrhage. Neurology 32:706–711; 1982.
24. Lee, K. Alcoholism and cerebrovascular thrombosis in the young. Acta Neurol. Scand. 59:270–274; 1979.
25. Nishio, A.; Gebrewold, A.; Altura, B. T.; Altura B. M. Comparative vasodilator effects of magnesium salts on rat mesenteric arterioles and venules. Arch. Intern. Pharmacodyn. Ther. 298:139–163; 1989.
26. Pritchard, J. A.; Cunningham, F. G.; Pritchard, S. A. The Parkland Memorial Hospital protocol for treatment of eclampsia: Evaluation of 245 cases. Am. J. Obstetr. Gynecol. 148:951–963; 1984.
27. Rasmussen, H. S.; Thomsen, P. E. B. The electrophysiological effects of intravenous magnesium on human sinus node, atrioventricular node, atrium and ventricle. Clin. Cardiol. 12:85–90; 1984.
28. Rivera, L. I.; Gootman, P.M.; Lin, R. H.; Gootman, N. Effects of elevated plasma magnesium concentration on cerebrospinal fluid levels of magnesium in neonatal swine. Proc. Soc. Exp. Biol. med. 197:98–101; 1991.
29. Turiapaty, P. D. M. V.; Altura, B. M. Extracellular magnesium ions control calcium exchange and content of vascular smooth muscle. Eur. I. Pharmacol. 52:421–423; 1978.
30. Zhang, A.; Altura, B. T.; Altura, B. M. Ethanol-induced contraction of cerebral arteries in diverse mammals and its mechanism of action. Eur. J. Pharmacol. 248:229–236; 1993.
31. Zhang, A.; Cheng, T. P. O.; Altura, B. M. $Mg^{2+}$ and caffeine-induced intracellular $Ca^{2+}$ release in human vascular endothelial cells. Br. J. Pharmacol. 109:291–292; 1993.

We claim:

1. A method of inducing a stroke in a mammal comprising:

administration of an amount of a hallucinogenic drug in combination with administration of an amount of a barbiturate, said amounts are sufficient to induce a stroke in the mammal.

2. The method according to claim 1 wherein said amounts are sufficient to result in a lower brain ionized magnesium concentration.

3. The method according to claim 1 wherein the hallucinogenic drug is selected from the group consisting of lysergic acid diethylamide, phencyclidine hydrochloride, an opioid, normorphine, morphine, amphetamine, methamphetamine, cannabinoid and derivatives thereof.

4. A method of inducing a stroke in a mammal consisting essentially of:

administration of an amount of a hallucinogenic drug, said amount is sufficient to induce a stroke in the mammal.

5. The method according to claim 4 wherein the hallucinogenic drug is selected from the group consisting of lysergic acid diethylamide, phencyclidine hydrochloride, an opioid, normorphine, morphine, amphetamine, methamphetamine, cannabinoid and derivatives thereof.

6. A method of inducing a stroke in a mammal comprising:

administration of an amount of a hallucinogenic drug in combination with administration of an amount of alcohol, said amounts are sufficient to induce a stroke in the mammal.

7. The method according to claim 6 wherein said amounts are sufficient to result in a low brain ionized magnesium concentration.

8. The method according to claim 6 wherein the hallucinogenic drug is selected from the group consisting of lysergic acid diethylamide, phencyclidine hydrochloride, an opioid, normorphine, morphine, amphetamine, methamphetamine, cannabinoid and derivatives thereof.

9. A method of inducing a stroke in a mammal consisting essentially of:

administration of an amount of alcohol, said amount is sufficient to induce a stroke in the mammal.

10. The method according to claim 9 wherein said amount is sufficient to result in a low brain ionized magnesium concentration.

11. A method of inducing a stroke in a mammal comprising:

administration of an amount of alcohol in combination with administration of an amount of cocaine or derivatives thereof, said amounts are sufficient to induce a stroke in the mammal.

12. A method according to claim 11 wherein said amounts are sufficient to result in a low brain ionized magnesium concentration.

13. A method of inducing a stroke in a mammal consisting essentially of:

administration of an amount of cocaine or derivatives thereof, said amount is sufficient to induce a stroke in the mammal.

14. A method according to claim 13, wherein said amount is sufficient to result in a low brain ionized magnesium concentration.

15. The method according to claims 1, 4, 6, 9, 11 or 13 wherein the administration is by a route selected from the group consisting of: intravenous, intramuscular, intraperitoneal, intracranial, intradermal and subcutaneous.

* * * * *